(12) United States Patent
Kallmes

(10) Patent No.: US 10,398,485 B2
(45) Date of Patent: Sep. 3, 2019

(54) BONE EXPANSION DEVICES AND METHODS

(71) Applicant: Mayo Foundation for Medical Education and Research, Rochester, MN (US)

(72) Inventor: David F. Kallmes, Rochester, MN (US)

(73) Assignee: KyphEZE, Inc., Rochester, MN (US)

( * ) Notice: Subject to any disclaimer, the term of this patent is extended or adjusted under 35 U.S.C. 154(b) by 0 days.

(21) Appl. No.: 15/744,479

(22) PCT Filed: Apr. 13, 2016

(86) PCT No.: PCT/US2016/027300
§ 371 (c)(1),
(2) Date: Jan. 12, 2018

(87) PCT Pub. No.: WO2017/011043
PCT Pub. Date: Jan. 19, 2017

(65) Prior Publication Data
US 2018/0199971 A1 Jul. 19, 2018

Related U.S. Application Data

(60) Provisional application No. 62/192,847, filed on Jul. 15, 2015.

(51) Int. Cl.
*A61B 17/58* (2006.01)
*A61B 17/60* (2006.01)
*A61F 2/00* (2006.01)
*A61B 17/88* (2006.01)
*A61M 25/10* (2013.01)

(52) U.S. Cl.
CPC ...... *A61B 17/8855* (2013.01); *A61B 17/8802* (2013.01); *A61B 17/8858* (2013.01); *A61M 25/1002* (2013.01)

(58) Field of Classification Search
CPC combination set(s) only.
See application file for complete search history.

(56) References Cited

U.S. PATENT DOCUMENTS

| | | |
|---|---|---|
| 6,648,854 B1 | 11/2003 | Patterson et al. |
| 2002/0177866 A1 | 11/2002 | Weikel et al. |
| 2008/0065139 A1 | 3/2008 | Scribner |
| 2008/0312637 A1* | 12/2008 | Miller ............... A61B 17/3472 604/512 |
| 2009/0299282 A1 | 12/2009 | Lau et al. |
| 2011/0251615 A1 | 10/2011 | Truckai |
| 2012/0016371 A1 | 1/2012 | O'Halloran |

(Continued)

OTHER PUBLICATIONS

PCT International Search Report and Written Opinion in International Appln. No. PCT/US2016/27300, dated Jul. 15, 2016, 12 pages.

(Continued)

*Primary Examiner* — Sameh R Boles

(57) ABSTRACT

Devices and methods for creating space within a body structure for therapeutic purposes include an expandable member disposed on the distal end portion of a catheter. Such devices and methods can be used, for example, for creating space within bone, and for injecting a filler material such as cement into the space to strengthen, repair, or otherwise enhance the bone structure.

20 Claims, 7 Drawing Sheets

(56) References Cited

U.S. PATENT DOCUMENTS

2012/0259375 A1   10/2012  Druma et al.
2014/0257311 A1    9/2014  Druma

OTHER PUBLICATIONS

PCT International Preliminary Report on Patentability in International Appln. No. PCT/US2016/27300, dated Jan. 16, 2018, 7 pages.

* cited by examiner

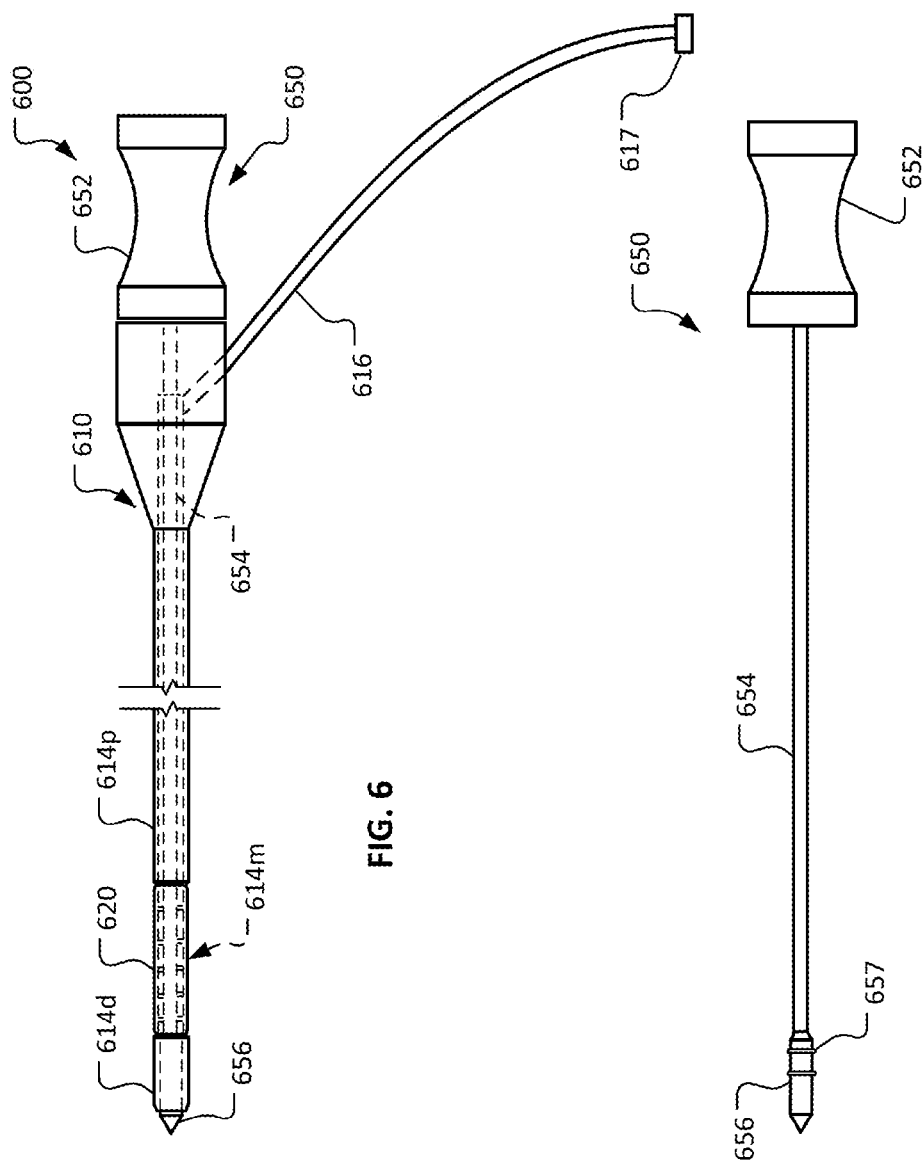

BONE EXPANSION DEVICES AND METHODS

CROSS REFERENCE TO RELATED APPLICATIONS

This application is a National Stage application under 35 U.S.C. § 371 of International Application No. PCT/US2016/027300, having an International Filing Date of Apr. 13, 2016, which claims the benefit of U.S. Provisional Application No. 62/192,847, filed Jul. 15, 2015. The disclosure of the prior application is applications are considered part of and are incorporated by reference in the disclosure of this application.

BACKGROUND

1. Technical Field

This document relates to devices and methods for creating space within a body structure for therapeutic purposes. For example, this document relates to orthopedic devices and methods for creating space within bone, and for injecting a filler material such as cement into the space to strengthen, repair, or otherwise enhance the bone structure.

2. Background Information

Cementoplasty pertains to percutaneous procedures including vertebroplasty, kyphoplasty, osteoplasty, and sacroplasty. In general, bone packing with cement aims to treat or prevent vertebral and extraspinal pathological fractures and relieve pain in patients with conditions such as osteoporosis and bone metastases.

Vertebroplasty and kyphoplasty are minimally invasive procedures for the treatment of painful vertebral compression fractures, which are fractures involving the vertebral bodies that make up the spinal column. In vertebroplasty, physicians use image guidance to inject a cement mixture into the fractured bone through a hollow needle. In kyphoplasty, a balloon is first inserted into the fractured bone through the hollow needle and then inflated to create a cavity or space. The cement is injected into the cavity once the balloon is removed.

Percutaneous osteoplasty, the injection of bone cement into a bone lesion refractory to conventional therapy (e.g., radiotherapy, chemotherapy, and narcotic analgesia), is performed to provide immediate bone structure consolidation, to reduce the risk of a pathological fracture, to achieve pain regression, and to improve mobility.

SUMMARY

This document provides devices and methods for creating space within a body structure for therapeutic purposes. For example, this document provides orthopedic devices and methods for creating space within bone, and for injecting a filler material such as cement into the space to strengthen, repair, or otherwise enhance the bone structure.

In one implementation, a needle-mounted balloon system includes a cannula and a stylet that is engageable with the cannula. The cannula includes a cannula hub, a cannula tube portion extending distally from the cannula hub and defining a lumen therethrough, and an expandable member coupled to the cannula tube portion. The expandable member is reconfigurable between a diametrically contracted configuration and a diametrically expanded configuration. The stylet includes a stylet hub and a stylet needle extending distally from the stylet hub. The stylet needle is slidably disposable within the lumen of the cannula tube portion. When the stylet is fully engaged with the cannula, a sharp distal tip portion of the stylet needle extends distally beyond the cannula tube portion.

Such a needle-mounted balloon system may optionally include one or more of the following features. The needle-mounted balloon system may also include an inflation tube coupled with the cannula and in fluid communication with the expandable member. The inflation tube may be coupled with the cannula hub. The cannula tube portion may define an inflation lumen that is in fluid communication with the expandable member and the inflation tube. In some embodiments, the expandable member is expandable only when the stylet is engaged with the cannula. In some embodiments, the expandable member is expandable when the stylet is engaged with the cannula and when the stylet is disengaged from the cannula. The needle-mounted balloon system may also include a connection member coupled with the cannula hub and in fluid communication with the lumen. The expandable member is a balloon device in various embodiments. The balloon device may be diametrically symmetrical. The balloon device may be diametrically asymmetrical. The needle-mounted balloon system may also include a second expandable member coupled to the cannula tube portion. In some embodiments, a distal-most portion of the cannula tube portion has a larger outer diameter than an outer diameter of the expandable member while the expandable member is in the diametrically contracted configuration.

In another implementation, a method for creating a space in a body structure and injecting a filler material into the space includes: (i) inserting a distal end portion of a needle-mounted balloon system into the body structure, (ii) reconfiguring the expandable member of the needle-mounted balloon system from the diametrically contracted configuration to the diametrically expanded configuration while the expandable member is in the body structure, (iii) reconfiguring the expandable member from the diametrically expanded configuration to the diametrically contracted configuration such that an open space is created in the body structure, and (iv) injecting a filler material into the open space.

Such a method for creating a space in a body structure and injecting a filler material into the space may optionally include one or more of the following features. The method may also include, prior to the injection of the filler material, removing the stylet from engagement with the cannula. In some embodiments, the body structure is bone. In some embodiments, the filler material is bone cement.

Particular embodiments of the subject matter described in this document can be implemented to realize one or more of the following advantages. In some embodiments, the devices and methods described herein provide enhanced ease-of-use in comparison to the devices and methods presently available for creating space within a body structure. For example, the devices and methods described herein may require fewer steps and fewer physical components. In addition to ease-of-use, the devices and methods described herein may reduce the amount of time required to perform a procedure. Further, with fewer components and a reduction in procedural times, a cost savings may be attained using the devices and methods provided herein. In use, the balloon device of the devices provided herein can be advantageously fully or partially inflated during the injection of filler material. Hence, the balloon device can be used to help achieve a desired placement of the filler material in the body cavity. In some embodiments, various conditions can be treated in a minimally invasive fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 1A is a cross-sectional view of an example cannula of the needle-mounted balloon system of FIG. 1. The cannula includes an inflation lumen and a lumen for a stylet.

FIG. 1B is an enlarged view of the distal end portion of the needle-mounted balloon system of FIG. 1.

FIG. 6 is a side view of another example needle-mounted balloon system for bone expansion in accordance with some embodiments provided herein. The needle-mounted balloon system is shown with its balloon in a contracted configuration.

FIG. 7 is a side view of a stylet that can be used with the needle-mounted balloon system of FIG. 6.

Like reference numbers represent corresponding parts throughout.

DETAILED DESCRIPTION

This document provides devices and methods for creating space within a body structure for therapeutic purposes. For example, this document provides orthopedic devices and methods for creating space within bone, and for injecting a filler material such as cement into the space to strengthen, repair, or otherwise enhance the bone structure.

Traditional systems for creating space within bone include a cannula and a separate balloon device that can be inserted via the cannula. First, the cannula is inserted so that its distal tip is located at a target area. Then the balloon device is introduced through a lumen of the cannula. After creating or enlarging a space by inflating the balloon device, the balloon device is then removed. Subsequently, a filler material, such as bone cement, is injected into the space via the cannula.

The devices and methods provided herein significantly improve upon the traditional systems and methods for creating space within a body (such as bone) by combining the cannula and balloon device into a single component. Accordingly, as described further below, the devices are easier and less time-consuming for a clinician to use. It should be understood that while the devices provided herein may be termed as "needle-mounted balloon systems," the devices can also be considered "cannula-mounted balloon systems."

Figure 1:
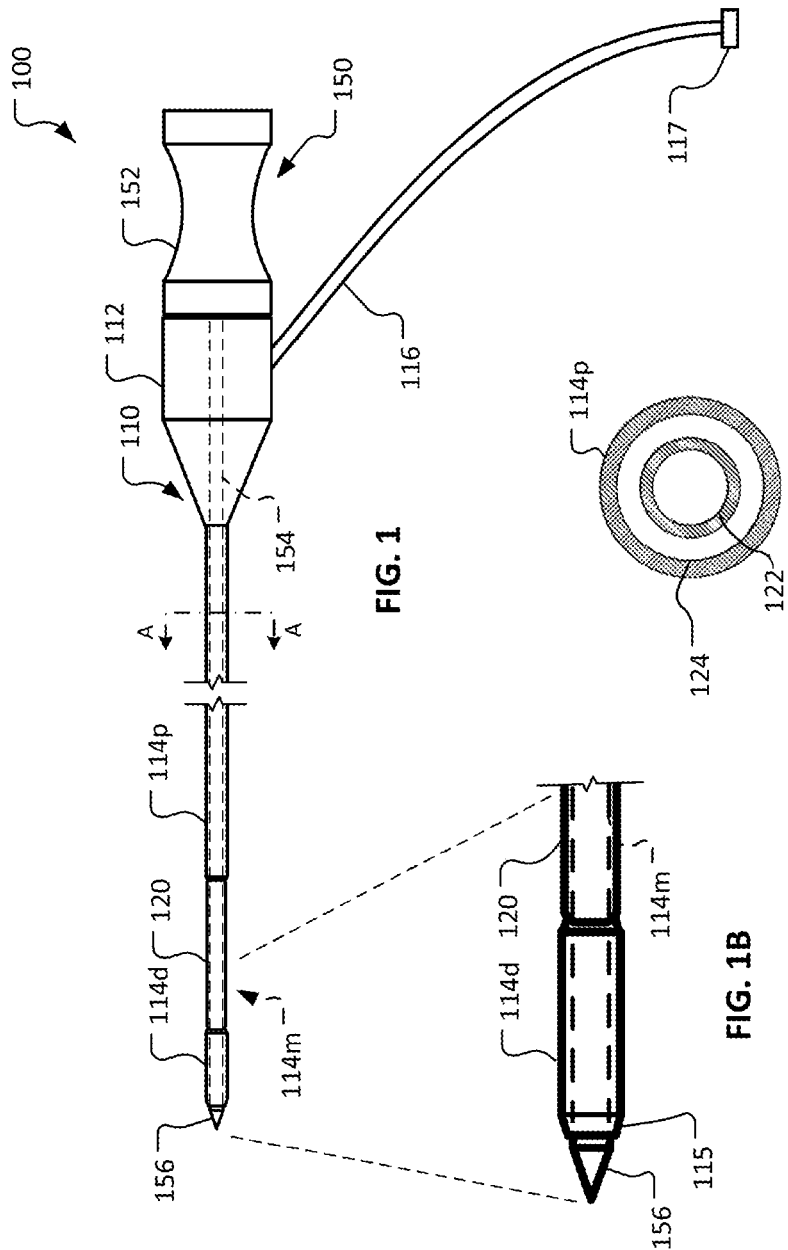
FIG. 1 is a side view of an example needle-mounted balloon system for bone expansion in accordance with some embodiments provided herein. The needle-mounted balloon system is shown with its balloon in a contracted/deflated configuration.

Referring to FIG. 1, an example needle-mounted balloon system 100 for bone expansion includes a cannula 110 and a stylet 150. Stylet 150 is slidably received within a lumen of the cannula 110. When stylet 150 is fully engaged with cannula 100, a sharp distal tip portion 156 of stylet 150 projects distally beyond a distal cannula tube portion 114d of cannula 110.

Figure 3:
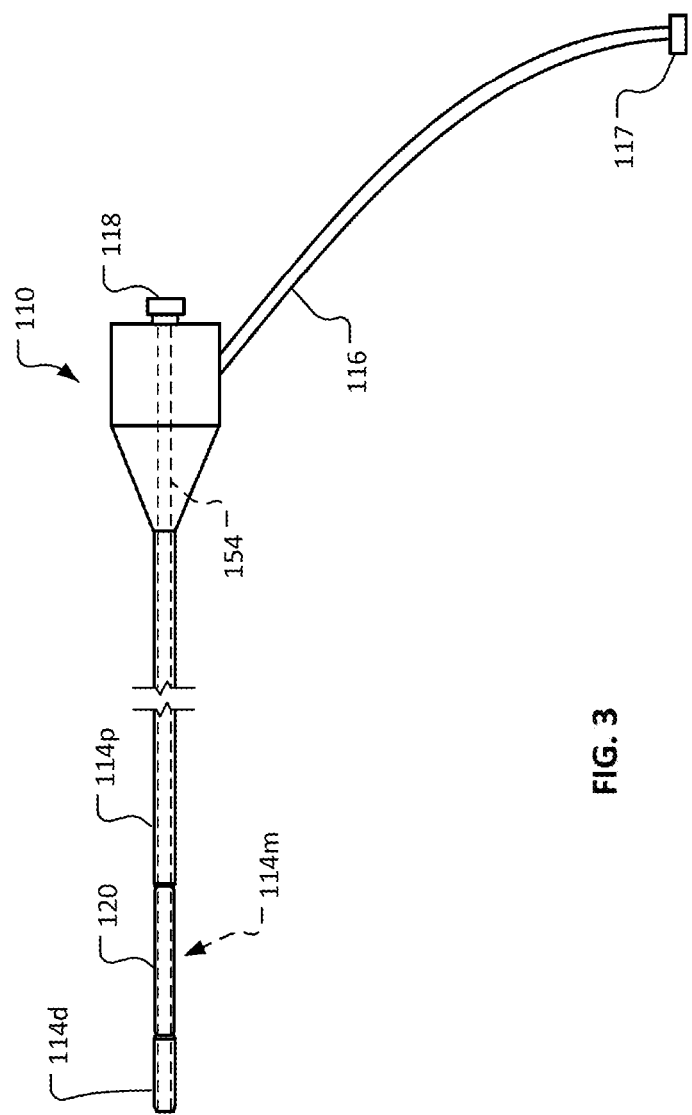
FIG. 3 is a side view of the example needle-mounted balloon system for bone expansion of FIG. 1. The needle-mounted balloon system is shown with its stylet removed.

In the depicted embodiment, cannula 110 includes a cannula hub 112, a proximal cannula tube portion 114p, a mid-body cannula tube portion 114m, an expandable member 120, distal cannula tube portion 114d, an inflation tube 116, and a connection member 118 (refer to FIG. 3). Cannula hub 112 is disposed at or near a proximal end of cannula 110. Proximal cannula tube portion 114p is coupled with cannula hub 112, and extends distally from cannula hub 112.

Referring also to FIG. 1A, proximal cannula tube portion 114p defines a main lumen 122 in which stylet 150 is slidably received. Additionally, in some embodiments proximal cannula tube portion 114p defines or includes one or more inflation lumens 124 (e.g., in the wall of proximal cannula tube portion 114p) through which an inflation media used for inflating expandable member 120 can flow. It should be understood that any of many different multi-lumen cannula designs can be used for proximal cannula tube portion 114p without departing from the scope of the disclosure. Alternatively, or additionally, in some embodiments such an inflation lumen may be provided by a separate tube.

In some embodiments, inflation tube 116 is also coupled with cannula hub 112. Alternatively, inflation tube 116 can bypass cannula hub 112 and be directly connected to proximal cannula tube portion 114p, the aforementioned inflation lumen, or expandable member 120. In the depicted embodiment, inflation tube 116 is in fluid communication with expandable member 120 via cannula hub 112 and/or the aforementioned inflation lumen.

When a source of inflation fluid (e.g., saline, radiographic contrast material, or a combination of both) is coupled with inflation tube 116 (e.g., via a connection 117), expandable member 120 can be inflated or deflated by pressurizing or depressurizing the source of inflation fluid. In some cases (without limitation), a syringe is used as the source of the inflation fluid. In some embodiments, a stopcock valve or other type of fluid control device can be used in conjunction with, or as an alternative to, connection 117. In some embodiments, connection 117 is a luer or luer-lock fitting.

Proximal cannula tube portion 114p extends distally from cannula hub 112. In some embodiments, proximal cannula tube portion 114p is metallic (e.g., stainless steel, nitinol, and the like). In some embodiments, proximal cannula tube portion 114p is made of a suitable biocompatible polymeric material. Proximal cannula tube portion 114p may be sized to any suitable length and diameter. For example, in some embodiments the outer diameter of proximal cannula tube portion 114p (without limitation) is in a range from about 2.4 mm to about 4.0 mm, or about 2.0 mm to about 3.0 mm, or about 1.5 mm to about 3.5 mm, or about 1.0 mm to about 2.5 mm, or any other suitable size. In some embodiments, the length of proximal cannula tube portion 114p (without limitation) is in a range from about 2.0 cm to about 4.0 cm, or about 3.0 cm to about 5.0 cm, or about 4.0 cm to about 6.0 cm, or about 5.0 cm to about 7.0 cm, or about 6.0 cm to about 8.0 cm, or about 7.0 cm to about 9.0 cm, or about 8.0 cm to about 10.0 cm, about 10.0 cm to about 15.0 cm, about 15.0 cm to about 20.0 cm, or greater than 20 cm, or any other suitable length.

Mid-body cannula tube portion 114m extends distally from proximal cannula tube portion 114p. In some embodiments, expandable member 120 is mounted on or around mid-body cannula tube portion 114m. Mid-body cannula tube portion 114m may have a smaller outer diameter than proximal cannula tube portion 114p, in some embodiments. In some such embodiments, the combined outer diameter of expandable member 120 (in its contracted configuration as shown) on mid-body cannula tube portion 114m is about the same diameter as, or a little smaller than, the outer diameter of proximal cannula tube portion 114p. In some such embodiments, the combined outer diameter of expandable member 120 (in its contracted configuration as shown) on mid-body cannula tube portion 114m is larger than the outer diameter of proximal cannula tube portion 114p.

In the depicted embodiment, distal cannula tube portion 114d extends distally from mid-body cannula tube portion 114m. Distal cannula tube portion 114d is optional. In some embodiments, no distal cannula tube portion 114d is included as part of needle-mounted balloon system 100. Instead, expandable member 120 and/or mid-body cannula tube portion 114m may be the distal-most portion of needle-mounted balloon system 100. In some embodiments, such as the depicted embodiment, that include distal cannula tube portion 114d, distal cannula tube portion 114d may have a length in a range of about 1.0 mm to about 6.0 mm, or about 4.0 mm to about 9.0 mm, or about 7.0 mm to about 12.0 mm, or about 10.0 mm to about 15.0 mm, or about 13.0 mm to about 18.0 mm, or about 16.0 mm to about 21.0 mm, or about 19.0 mm to about 24.0 mm, or about 22.0 mm to about 25.0 mm, or greater than 25.0 mm (e.g., about 3 cm, about 4 cm, about 5 cm, and the like). In some embodiments the outer diameter of distal cannula tube portion 114d (without limitation) is in a range from about 2.4 mm to about 4.0 mm, or about 2.0 mm to about 3.0 mm, or about 1.5 mm to about 3.5 mm, or about 1.0 mm to about 2.5 mm, or any other suitable size. While in some embodiments the outer diameter of distal cannula tube portion 114d is the same as the outer diameter of proximal cannula tube portion 114p, in some embodiments the outer diameters of distal cannula tube portion 114d and proximal cannula tube portion 114p are dissimilar.

Referring also to FIG. 1B, in some embodiments (such as the depicted embodiment), the outer diameter of distal cannula tube portion 114d is larger than the outer diameter of expandable member 120 (in its contracted configuration as shown). In addition, in some embodiments the outer diameter of distal cannula tube portion 114d is larger than the outer diameter of proximal cannula tube portion 114p. Hence, with the outer diameter of the distal cannula tube portion 114d being larger than the outer diameter of the expandable member 120, the distal cannula tube portion 114d can provide protection for the expandable member 120 during insertion into the body. That is, distal cannula tube portion 114d can absorb the stresses associated with tunneling into the body structure (e.g., bone, cartilage, other tissues, etc.), so that expandable member 120 is not subjected to such stresses. Moreover, the distal leading-end 115 of distal cannula tube portion 114d can be tapered or beveled as shown. Such a taper (along with the pointed tip of stylet 150) can help facilitate the insertion of needle-mounted balloon system 100 with less force required and less trauma induced.

In some embodiments, one or more radiopaque markers are included on one or more locations on proximal cannula tube portion 114p, mid-body cannula tube portion 114m, and/or distal cannula tube portion 114d.

Example needle-mounted balloon system 100 also includes expandable member 120. In the depicted embodiment, expandable member 120 is a balloon device affixed to cannula 110. Expandable member 120 is reconfigurable between a contracted configuration and a diametrically expanded configuration by pressurizing expandable member 120 using an inflation fluid. In some embodiments, the length of expandable member 120 (without limitation) is in a range from about 10.0 mm to about 12.0 mm, or about 11.0 mm to about 13.0 mm, or about 12.0 mm to about 14.0 mm, or about 13.0 mm to about 15.0 mm, or about 14.0 mm to about 16.0 mm, or about 15.0 mm to about 17.0 mm, or about 16.0 mm to about 18.0 mm, about 17.0 mm to about 19.0 mm, about 18.0 mm to about 20.0 mm, about 19.0 mm to about 22.0 mm, about 20.0 mm to about 24.0 mm, about 22.0 mm to about 26.0 mm, about 24.0 mm to about 30.0 mm, or greater than 30 mm, or any other suitable length.

In some embodiments, expandable member 120 is made of a material and structured to have a high burst pressure (e.g., about 20 atmospheres, about 30 atmospheres, about 40 atmospheres, or more). Expandable member 120 can be made of materials such as, but not limited to, flexible polyvinyl chloride (PVC), polyester (PET), Nylons, Pebax, polyurethane, polyurethanes blends, and the like, and combinations thereof. Expandable member 120 can be made with a single layer, dual layers, or more than two layers of material.

In some embodiments, an optional protective sleeve or shell (not shown) is included that surrounds expandable member 120 (in its contracted configuration). The sleeve can serve to protect expandable member 120 during insertion of cannula 110. Then, in some embodiments, inflation of expandable member 120 can fracture the sleeve so that expandable member 120 can inflate to its expanded configuration. Alternatively, in some embodiments the clinician-user can retract the protective sleeve prior to inflation of expandable member 120.

In some embodiments, one or more radiopaque markers are included on one or more locations on expandable member 120.

Example needle-mounted balloon system 100 also includes stylet 150. Stylet 150 includes a stylet hub 152 and a needle 154 that extends distally from stylet hub 152. In the depicted embodiment, stylet 150 is slidably disposed within cannula 110 such that hub 152 extends proximally from cannula hub 112. Stylet hub 152 can be configured for convenient manual gripping by a clinician.

A sharp distal tip portion 156 extends distally beyond the extreme distal end of cannula 110 when stylet 150 is fully engaged within cannula 110. The sharp distal tip portion 156 can be configured with various styles of tips such as, but not limited to, cone, bevel, dual gauge, and the like.

Stylet 150 serves to make the insertion of cannula 110 more safe and effective. For example, stylet 150 includes sharp distal tip portion 156 which is suitable for piercing tissues as needle-mounted balloon system 100 is being inserted. Additionally, stylet 150 provides or supplements the column strength of needle-mounted balloon system 100 so that cannula 110 can be inserted to a target area of the patient's anatomy. In some embodiments, stylet 150 is malleable so that a clinician can form stylet 150 into a curved shape if so desired.

In some embodiments, stylet 150 is made of a metallic material such as, but not limited to, stainless steel, stainless steel alloys, nitinol, titanium, titanium alloys, and the like. In some embodiments, stylet 150 is made of a polymeric material.

Figure 2:
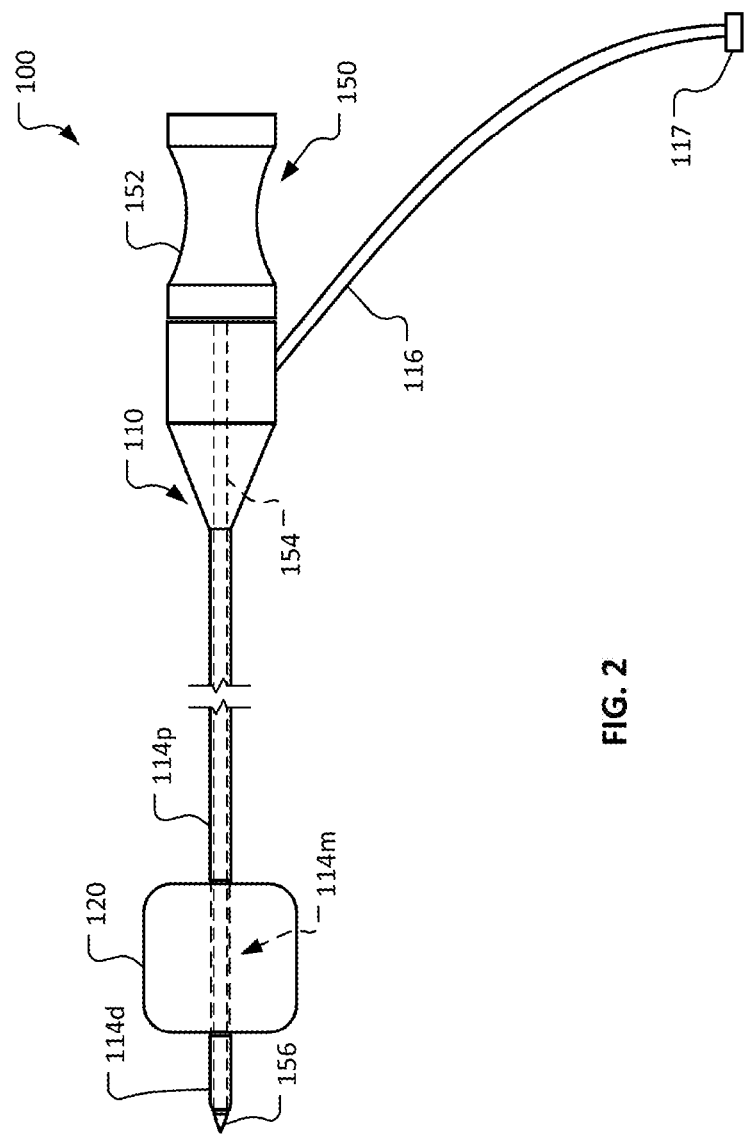
FIG. 2 is a side view of the example needle-mounted balloon system for bone expansion of FIG. 1. The needle-mounted balloon system is shown with its balloon in an expanded/inflated configuration.

Referring also FIG. 2, expandable member 120 of example needle-mounted balloon system 100 can be configured in an expanded configuration as shown in FIG. 2. In the depicted embodiment, expandable member 120 can be inflated to the diametrically symmetrical expanded configuration by pressurizing expandable member 120 using an inflation fluid as described above.

In some embodiments, the expanded outer diameter of expandable member 120 (without limitation) is in a range of about 8 mm to about 10 mm, about 9 mm to about 11 mm, about 10 mm to about 12 mm, about 11 mm to about 13 mm, about 12 mm to about 14 mm, about 13 mm to about 15 mm, about 14 mm to about 16 mm, about 15 mm to about 17 mm, about 16 mm to about 18 mm, about 17 mm to about 19 mm, about 18 mm to about 20 mm, about 19 mm to about 21 mm, or greater than 21 mm.

In some embodiments, a radiopaque solution is used as the inflation media for expandable member 120. In some embodiments, another type of fluid (e.g., saline) is used as the inflation media.

After inflating expandable member 120 to the expanded configuration, in some embodiments expandable member 120 can be deflated so that expandable member 120 returns to, or near to, the contracted configuration as shown in FIG. 1.

Referring to also FIG. 3, stylet 150 can be slidably removed from engagement with cannula 110. When stylet 150 is removed from cannula 110 (as shown in FIG. 3), connection member 118 is accessible. In some embodiments, connection member 118 is a luer or luer-lock fitting. In some embodiments, connection member 118 includes a valve, septum, or another type of fitting.

Connection member 118 is in fluid communication with the lumen of cannula 110 (i.e., the lumen previously occupied by stylet 150). Accordingly, a filler material (e.g., bone cement, or another type of flow-able material) can be injected via cannula 110 by connecting a filler material source to connection member 118 and pressurizing the filler material. In result, filler material will flow out from distal cannula tube portion 114d. In some implementations, as described further below in reference to FIG. 8, filler material that is injected via cannula 110 will fill a space that was previously created or enlarged by the expansion of expandable member 120.

Figure 4:
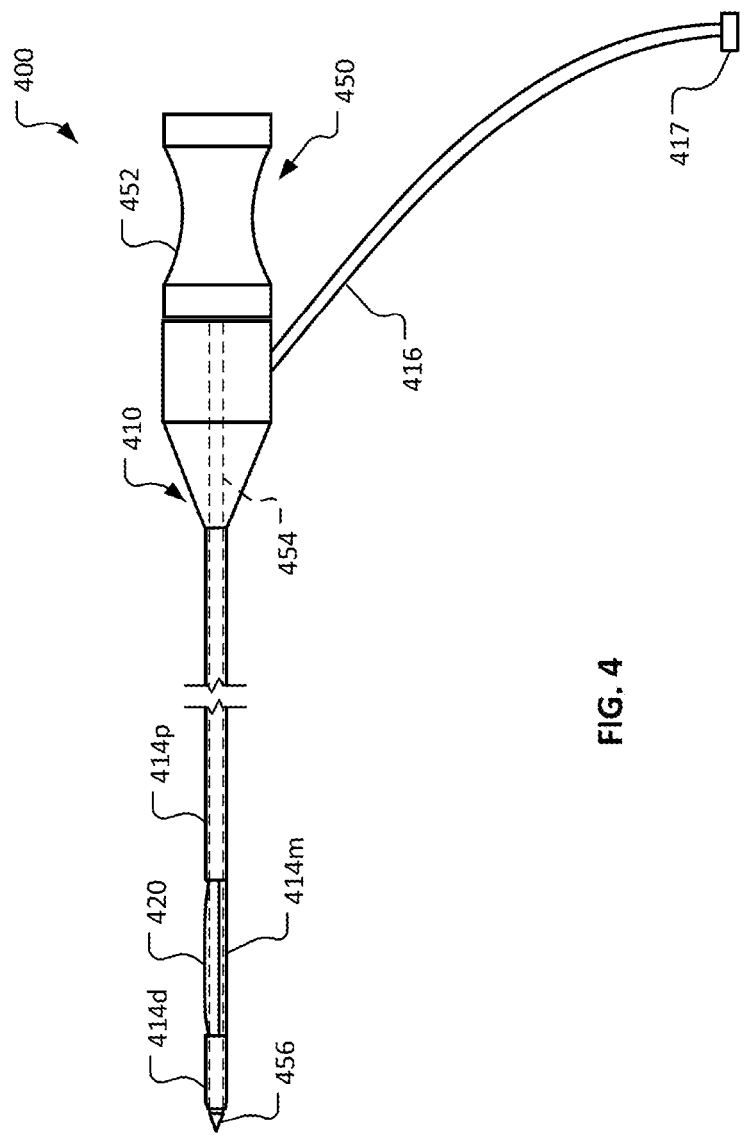
FIG. 4 is a side view of another example needle-mounted balloon system for bone expansion in accordance with some embodiments provided herein. The needle-mounted balloon system is shown with its balloon in a contracted configuration.
Figure 5:
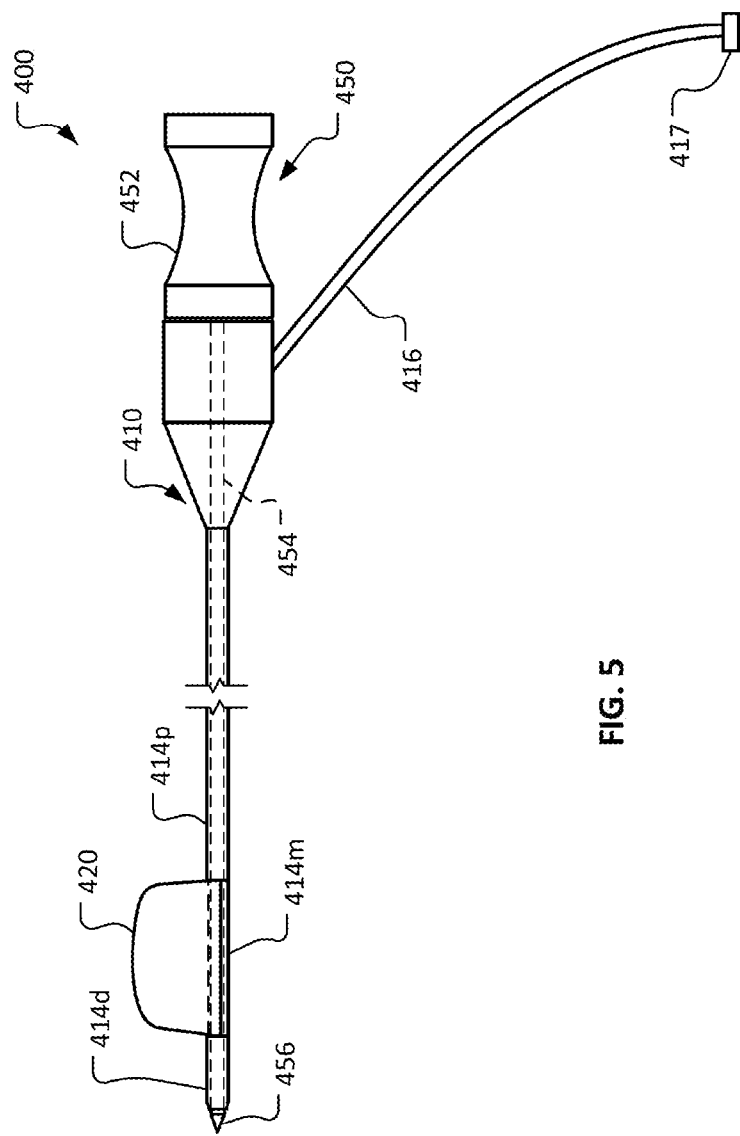
FIG. 5 is a side view of the example needle-mounted balloon system for bone expansion of FIG. 5. The needle-mounted balloon system is shown with its balloon in an expanded configuration.

Referring to FIGS. 4 and 5, an example needle-mounted balloon system 400 is configured like needle-mounted balloon system 100, except that needle-mounted balloon system 400 includes a diametrically asymmetrical expandable member 420. Asymmetrical expandable member 420 is shown in its contracted configuration in FIG. 4 and in its expanded configuration in FIG. 5.

It should be understood that the expandable members of the needle-mounted balloon system provided herein can be selected to have any desirable shape, size, configuration, material, and other properties.

In some embodiments, the needle-mounted balloon systems provided herein can include two or more expandable members that may be either independently or collectively inflatable. In some such embodiments, one or more of the expandable members can be configured to provide a seal to contain injected filler material within the space being filled. In one such example, a cannula of a needle-mounted balloon system includes two balloons that are individually inflatable and deflatable. The two balloons can be arranged generally adjacent to each other, with a first balloon being a distal balloon and a second balloon being a proximal balloon (located proximally of the first balloon). After inserting the balloons into the target body structure, both balloons can be inflated. Then, the distal balloon can be deflated while the proximal balloon remains inflated. Then, the filler material can be injected to fill the space previously occupied by the expanded distal balloon. While the filler material is filling the space, the inflated proximal balloon acts as a seal or a dam to help ensure that the filler material is contained only in the space previously occupied by the expanded distal balloon.

Referring to FIGS. 6 and 7, an example needle-mounted balloon system 600 can include a stylet 650 with a mid-body portion 654 that is configured to provide a space for an inflation fluid to flow within the lumen of cannula 610 from cannula hub 612 to expandable member 620. A distal end portion 656 of stylet 650 can be larger such that distal end portion 656 slidably seals with the lumen of cannula 610. Accordingly, when a source of inflation fluid (e.g., saline) is coupled with inflation tube 616 (e.g., via a connection 617), expandable member 620 can be inflated or deflated by pressurizing or depressurizing the source of inflation fluid.

Mid-body portion 654 defines a one or more openings that allow passage of the inflation fluid between the lumen of cannula 610 and the interior of expandable member 620. In this configuration, the expandable member 620 is only expandable when the stylet 650 is engaged with the cannula 610.

In some embodiments, one or more compliant sealing members 657 (e.g., O-rings) are disposed between the inner diameter of distal cannula tube portion 614d and the outer diameter of distal end portion 656 of stylet 650. Such compliant sealing member(s) 657 can help ensure that the pressurized inflation fluid is directed solely into expandable member 620, and can help maintain the pressure of the inflation fluid in expandable member 620 while expandable member 620 is inflated.

The configuration of example needle-mounted balloon system 600 eliminates the need for an inflation lumen between cannula hub 612 and expandable member 620, thereby simplifying the overall design. Therefore, needle-mounted balloon system 600 may be particularly cost effective to manufacture and/or convenient to operate.

Figure 8:
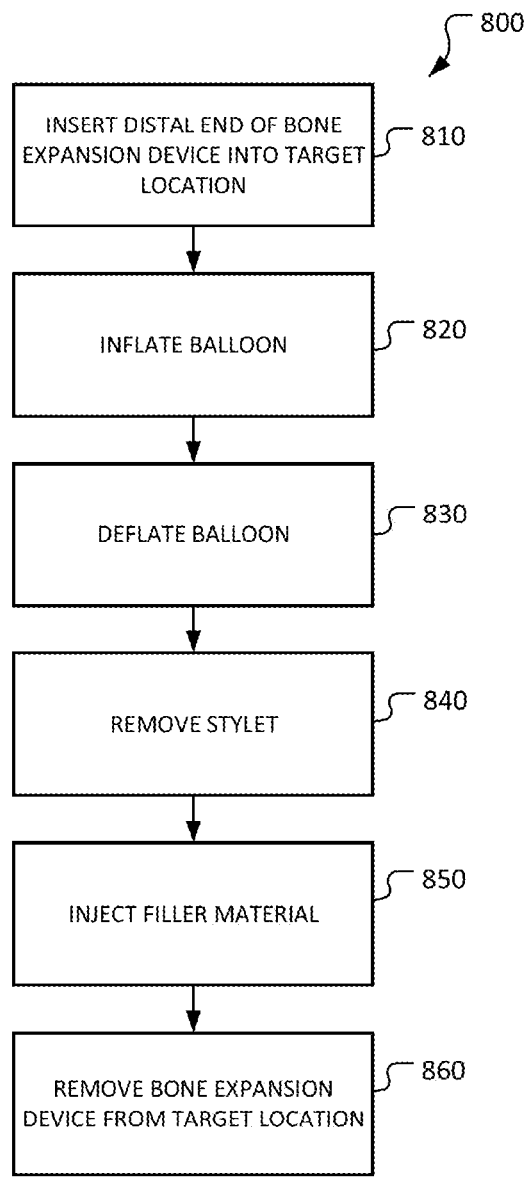
FIG. 8 is flowchart of a method for creating a space in a body and injecting a filler material into the space, using the needle-mounted balloon systems for bone expansion provided herein, in accordance with some embodiments.

Referring to FIG. 8, a method 800 for creating a space and injecting a filler material (e.g., a cementoplasty method), using the needle-mounted balloon systems for bone expansion provided herein, is depicted in a flowchart.

At step 810, at least a distal end portion of a needle-mounted balloon system (e.g., as described above) is inserted to a target location. In some embodiments, this step is performed using fluoroscopy or another type of imaging modality. Optionally, after completion of step 810, the stylet of the needle-mounted balloon system can be removed from the cannula of the needle-mounted balloon system.

At step 820, a balloon device of the needle-mounted balloon system is inflated to expand the diameter of the balloon device. For example, a source of inflation fluid can be connected to the needle-mounted balloon system and activated to pressurize the balloon device. In result, the expanded balloon device may create a space at the target location as desired. Optionally, after completion of step 820, the stylet of the needle-mounted balloon system can be removed from the cannula of the needle-mounted balloon system.

At step 830, the balloon device of the needle-mounted balloon system is deflated to contract the diameter of the balloon device. For example, the source of inflation fluid can be activated to depressurize the balloon device. In result, when the balloon device has been deflated, the space previously occupied by the balloon device at the target location may at least partially remain.

At step 840, the stylet of the needle-mounted balloon system is removed from the cannula of the needle-mounted balloon system (unless it was previously removed). The resulting configuration of the cannula is shown, for example, in FIG. 3. It should be understood that for example needle-mounted balloon system 600, the stylet cannot be removed until step 840. However, for the other embodiments of needle-mounted balloon systems, the stylet can optionally be removed any time after the completion of step 810 and prior to step 850.

At step 850, filler material (e.g., bone cement or other flow-able material) is injected to the space via the cannula of the needle-mounted balloon system. For example, as described above in reference to FIG. 3, a source of filler material can be connected to a connection member of the cannula, and the filler material can be pressurized to make it flow out from a distal portion of the cannula and into the space. The space may be partially or substantially completely filled by the filler material.

At step 860, the needle-mounted balloon system is retracted from the target location. In some embodiments, process 800 may be repeated in another location that is near to, or adjacent to, the target location. When the needle-mounted balloon system has been retracted, the filler material remains within the space at the target location. For example, in some implementations bone cement remains within the space created by the expanded balloon device within the bone structure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A needle-mounted balloon system comprising: a cannula comprising: a cannula hub; a cannula tube portion extending distally from the cannula hub, the cannula tube portion defining a lumen therethrough; and an expandable member coupled to the cannula tube portion, the expandable member being reconfigurable between a diametrically contracted configuration and a diametrically expanded configuration; and a stylet that is engageable with the cannula, the stylet comprising: a stylet hub; and a stylet needle extending distally from the stylet hub, wherein the stylet needle is slideably disposable within the lumen of the cannula tube portion, wherein, when the stylet is fully engaged with the cannula, a sharp distal tip portion of the stylet needle extends distally beyond the cannula tube portion, and wherein the expandable member is expandable when the stylet is at least one of engaged with the cannula and when the stylet is disengaged from the cannula.

2. The needle-mounted balloon system of claim 1, further comprising an inflation tube coupled with the cannula and in fluid communication with the expandable member.

3. The needle-mounted balloon system of claim 2, wherein the inflation tube is coupled with the cannula hub.

4. The needle-mounted balloon system of claim 2, wherein the cannula tube portion defines an inflation lumen, and wherein the inflation lumen is in fluid communication with the expandable member and the inflation tube.

5. The needle-mounted balloon system of claim 1, wherein the expandable member is expandable only when the stylet is engaged with the cannula.

6. The needle-mounted balloon system of claim 1, further comprising a connection member coupled with the cannula hub and in fluid communication with the lumen.

7. The needle-mounted balloon system of claim 1, wherein a distal-most portion of the cannula tube portion has a larger outer diameter than an outer diameter of the expandable member while the expandable member is in the diametrically contracted configuration.

8. A needle-mounted balloon system comprising:
a cannula comprising: a cannula hub; a cannula tube portion extending distally from the cannula hub, the cannula tube portion defining a lumen therethrough; and
a balloon coupled to the cannula tube portion, the balloon being reconfigurable between a diametrically contracted configuration and a diametrically expanded configuration, wherein the balloon is at least one of diametrically symmetrical and diametrically asymmetrical; and a stylet that is engageable with the cannula, the stylet comprising: a stylet hub; and a stylet needle extending distally from the stylet hub, wherein the stylet needle is slideably disposable within the lumen of the cannula tube portion, and wherein, when the stylet is fully engaged with the cannula, a sharp distal tip portion of the stylet needle extends distally beyond the cannula tube portion.

9. The needle-mounted balloon system of claim 8, wherein the balloon is diametrically symmetrical.

10. The needle-mounted balloon system of claim 8, wherein the balloon is diametrically asymmetrical.

11. The needle-mounted balloon system of claim 8, wherein the balloon is a first balloon, the system comprising a second balloon coupled to the cannula tube portion.

12. The needle-mounted balloon system of claim 8, further comprising an inflation tube coupled with the cannula and in fluid communication with the balloon.

13. The needle-mounted balloon system of claim 12, wherein the inflation tube is coupled with the cannula hub.

14. The needle-mounted balloon system of claim 12, wherein the cannula tube portion defines an inflation lumen, and wherein the inflation lumen is in fluid communication with the balloon and the inflation tube.

15. A needle-mounted balloon system comprising:
a cannula comprising: a cannula hub; a cannula tube portion extending distally from the cannula hub, the cannula tube portion defining a lumen therethrough; and a first expandable member coupled to the cannula tube portion, the first expandable member being reconfigurable between a diametrically contracted configuration and a diametrically expanded configuration; and a second expandable member coupled to the cannula tube portion; and a stylet that is engageable with the cannula, the stylet comprising: a stylet hub; and a stylet needle extending distally from the stylet hub, wherein the stylet needle is slideably disposable within the lumen of the cannula tube portion, wherein, when the stylet is fully engaged with the cannula, a sharp distal tip portion of the stylet needle extends distally beyond the cannula tube portion.

16. The needle-mounted balloon system of claim 15, wherein the first expandable member defines a first balloon.

17. The needle-mounted balloon system of claim 15, wherein the second expandable member defines a second balloon.

18. The needle-mounted balloon system of claim 15, further comprising an inflation tube coupled with the cannula and in fluid communication with the first expandable member.

19. The needle-mounted balloon system of claim 18, wherein the inflation tube is coupled with the cannula hub.

20. The needle-mounted balloon system of claim 15, further comprising a connection member coupled with the cannula hub and in fluid communication with the lumen.

\* \* \* \* \*